United States Patent
Reed et al.

(10) Patent No.: US 11,648,193 B2
(45) Date of Patent: *May 16, 2023

(54) PERSONAL CARE COMPOSITIONS

(71) Applicant: Colgate-Palmolive Company, New York, NY (US)

(72) Inventors: Jesse Reed, Flemington, NJ (US); Cheryl Kozubal, Somerset, NJ (US); Marian Holerca, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/480,284

(22) Filed: Sep. 21, 2021

(65) Prior Publication Data

US 2022/0000740 A1 Jan. 6, 2022

Related U.S. Application Data

(63) Continuation of application No. 16/066,805, filed as application No. PCT/US2015/068233 on Dec. 31, 2015, now Pat. No. 11,147,757.

(51) Int. Cl.
| | | |
|---|---|---|
| *C11D 1/02* | (2006.01) | |
| *C11D 1/29* | (2006.01) | |
| *C11D 1/88* | (2006.01) | |
| *C11D 1/94* | (2006.01) | |
| *A61K 8/20* | (2006.01) | |
| *A61K 8/365* | (2006.01) | |
| *A61K 8/368* | (2006.01) | |
| *A61Q 19/10* | (2006.01) | |
| *A61K 8/44* | (2006.01) | |
| *A61K 8/46* | (2006.01) | |
| *A61Q 5/02* | (2006.01) | |
| *A61Q 19/00* | (2006.01) | |

(52) U.S. Cl.
CPC ............. *A61K 8/442* (2013.01); *A61K 8/20* (2013.01); *A61K 8/365* (2013.01); *A61K 8/368* (2013.01); *A61K 8/44* (2013.01); *A61K 8/463* (2013.01); *A61Q 5/02* (2013.01); *A61Q 19/00* (2013.01); *A61Q 19/10* (2013.01); *A61K 2800/48* (2013.01); *A61K 2800/596* (2013.01)

(58) Field of Classification Search
CPC .... C11D 1/02; C11D 1/29; C11D 1/88; C11D 1/94; C11D 3/042; C11D 3/046; A61K 8/20; A61K 8/365; A61K 8/368; A61K 8/442; A61K 8/463; A61Q 19/10
See application file for complete search history.

(56) References Cited

U.S. PATENT DOCUMENTS

| | | | |
|---|---|---|---|
| 4,938,953 A | 7/1990 | Pena et al. | |
| 6,265,368 B1 | 7/2001 | Aronson et al. | |
| 6,361,768 B1 | 3/2002 | Galleguillos et al. | |
| 6,776,995 B1 | 8/2004 | Revivo | |
| 7,008,618 B1 | 3/2006 | Hessefort et al. | |
| 7,238,652 B2 | 7/2007 | Carnali et al. | |
| 7,758,851 B2 | 7/2010 | Urgell Beltran et al. | |
| 7,851,423 B2 | 12/2010 | Ruppert et al. | |
| 9,187,716 B2 | 11/2015 | Griffin et al. | |
| 9,409,853 B2 | 8/2016 | Schuch et al. | |
| 9,622,951 B2 | 4/2017 | Guskey et al. | |
| 10,391,046 B2 * | 8/2019 | Hartnett | A61K 8/042 |
| 11,147,757 B2 * | 10/2021 | Reed | A61Q 5/02 |
| 2003/0064091 A1 | 4/2003 | Kinderdine et al. | |
| 2004/0105894 A1 | 6/2004 | Gupta | |
| 2006/0079415 A1 | 4/2006 | Kozubal et al. | |
| 2012/0128618 A1 | 5/2012 | Claas et al. | |
| 2014/0121268 A1 * | 5/2014 | Guskey | A61Q 19/10 514/517 |
| 2015/0315123 A1 * | 11/2015 | Schuch | C07C 69/52 554/173 |

FOREIGN PATENT DOCUMENTS

| | | | | |
|---|---|---|---|---|
| CN | 104306222 | | 1/2015 | |
| DE | 19950019 | | 4/2001 | |
| DE | 102009026775 | | 12/2010 | |
| DE | 102011078111 | * | 5/2012 | ............... A61K 8/37 |
| DE | 102012220148 | | 5/2014 | |
| EA | 201170652 | | 2/2016 | |
| EP | 1674132 | | 6/2006 | |
| EP | 1932512 | | 6/2008 | |
| EP | 2066285 | | 6/2009 | |
| EP | 2069470 | | 5/2011 | |
| EP | 2559749 | | 2/2013 | |
| EP | 2881381 | | 6/2015 | |
| RU | 2170570 | | 7/2001 | |
| WO | 2003/051319 | | 6/2003 | |

(Continued)

OTHER PUBLICATIONS

Artyushenko, O., "Substances Regulating Viscosity", 2012, online request date Apr. 5, 2019: http://haircolor.org.ua/obshchie-ponyatiya/sovsem-chut-chut-nauki/ 91-veschestva-reguliruyuschie-vyazkost.html.

Bocca, B., et al. Toxic metals contained in cosmetics: a status report// Regul Toxicol Pharmacol, 2014, 68(3): 447-67, abstract.

International Search Report and Written Opinion of the International Searching Authority in International Application No. PCT/US2015/068233, dated Mar. 17, 2016.

1985, "Hair Care Products", Cosmetics & Toiletries, 100:81.

Beromin Chemie, 2015, "Iced Pineapple Shower Gel", Mintel Database GNPF AN: 3276963.

Caelo, 2015, "Safety data sheet of the commercial product", Texapon NSO, pp. 1-4.

(Continued)

*Primary Examiner* — Brian P Mruk

(57) ABSTRACT

A personal care composition comprising a surfactant system consisting essentially of an anionic surfactant and a zwitterionic surfactant; a preservative; a pH modifier; and a rheology modifier, wherein the ratio of anionic surfactant to zwitterionic surfactant is about 1:1 to about 2.2:1 of the total composition by weight.

10 Claims, No Drawings

(56) References Cited

FOREIGN PATENT DOCUMENTS

| WO | 2003/078558 | 9/2003 |
|---|---|---|
| WO | 2007/006402 | 1/2007 |
| WO | 2008/017653 | 2/2008 |
| WO | 2008/039440 | 4/2008 |
| WO | 2010/003860 | 1/2010 |
| WO | 2012/142407 | 10/2012 |
| WO | 2013/098066 | 7/2013 |
| WO | 2014/070689 | 5/2014 |
| WO | 2014/090651 | 6/2014 |
| WO | 2015/052021 | 4/2015 |
| WO | 2016/146361 | 9/2016 |

OTHER PUBLICATIONS

Carechemicals, 2006, Product Data Sheet TEXAPON, N 70.
Evonik Industries, 2003, "REWOPOL SB FA 30 B", pp. 1.
Evonik Industries, 2008, "REWOPOL SB FA 30 B", pp. 1-3.
Evonik Industries, 2008, "TEGO Betain F 50", pp. 1-4.
Fey et al., 1997, "Dictionary of cosmetics", pp. 194-195.
Fiume et al., 2020, "Safety Assessment of PEGylated Alkyl Glycerides as Used in Cosmetics", International Journal of Toxicology, 39(2):26S-58S.
Henkel KGaA, 1997, "Data Profile—DEHYTON PK45", pp. 1-5.
Hollis, 1995, "Sufactants Europa", A directory of Surface Active Agents available in Europe, The Royal Society of Chemistry, vol. 3.
Inolex, 2015, "Saftey Data Sheet", Lexaine C, pp. 1-6.
Kortemeier et al., 2010, "Thickening Agents for Surfactant Systems", SOFW Journal, 136:30-38.
Murakami et al., 2015, "Balancing Texture with Electrolyte Resistance for Improved Thickening", Cosmetics & Toiletries, pp. 1-15.
Umbach, 2004, "Kosmetik und Hygiene", pp. 1-3.
Weber, 2005, "New Alternatives to Paraben-based Preservative Blends", Cosmetic & Toiletries Magazine, 120(1):57-62.
Ziolkowsky, 1998, "Made for You Sympathetic Nonionic Ingredients for Personal Care", pp. 72-73.

* cited by examiner

PERSONAL CARE COMPOSITIONS

This application is a continuation of Ser. No. 16/066,805, filed on Jun. 28, 2018, now U.S. Pat. No. 11,147,757, which is a 371 of PCT/US2015/068233, filed on Dec. 31, 2015.

BACKGROUND

In recent years, foaming emulsions, particularly for shower gel products, have become increasingly popular in various areas of the world. These compositions can provide skin cleansing and caring in one application. In order for such compositions to be effective, one should have a physically stable composition with high foaming characteristics but which remains mild to the skin and provide an appropriate skin feel and conditioning effect during and after use. To meet the various demands and requirements for such compositions, many of the available products include a large number of ingredients. However, the complexity of such compositions requires great time and logistical effort, and is often very expensive to create.

Thus, it is desirable to have a composition having a simple formula without sacrificing the beneficial foaming, sensory, and rheological characteristics. Embodiments of the present invention are designed to meet these needs.

BRIEF SUMMARY

Some embodiments of the present invention provide a surfactant system comprising an anionic surfactant, such as, for example, sodium laureth sulfate, and a zwitterionic surfactant, such as, for example, cocoamidopropyl betaine, in a personal cleansing system comprising a preservative, a pH modifier and a rheology modifier provides a balance of desirable formulation properties. It has been surprisingly found that the compositions described herein unexpectedly provide beneficial foaming, sensory, and rheological characteristics even with a minimal number of ingredients.

Some embodiments provide a personal care composition comprising a surfactant system; a preservative; a pH modifier; and a rheology modifier, wherein the surfactant system consists essentially of an anionic surfactant and a zwitterionic surfactant, wherein the ratio of anionic surfactant to zwitterionic surfactant is about 1:1 to about 2.2:1 of the total composition by weight; and the composition is substantially free of other anionic surfactants; or of other zwitterionic surfactants.

In some embodiments, the present invention provides personal care compositions comprising a surfactant system consists essentially of cocoamidopropyl betaine and an anionic surfactant; a preservative; an effective amount of lactic acid; and sodium chloride, wherein the ratio of anionic surfactant to cocoamidopropyl betaine is about 1:1 to about 2.2:1.

Other embodiments provide a method of cleansing skin comprising the steps of applying to the skin a personal care composition as described herein.

DETAILED DESCRIPTION

Unless otherwise specified, all percentages and amounts expressed herein and elsewhere in the specification should be understood to refer to percentages by weight. The weight percentages as expressed herein are understood to refer to the percentage by weight of active components based on the total weight of a personal care composition as described herein. For example, for if 7.9 wt % of a 70% surfactant solution is employed in a given formulation as described herein, the % surfactant would be 5.53 wt % of the composition (i.e., the % of the active).

The term "about," when used in reference to a range of values, should be understood to refer to either value in the range, or to both values in the range. As used throughout, ranges are used as shorthand for describing each and every value that is within the range. Any value within the range can be selected as the terminus of the range.

The present disclosure provides personal care compositions comprising a simplistic formula that are storage stable. Preferably, the composition comprises water as a carrier. The composition may comprise a surfactant system having an anionic surfactant and a zwitterionic surfactant. The composition may further comprise a preservative, a pH modifier, and a rheology modifier.

In one exemplary embodiment, the present disclosure provides personal care composition (Composition 1) consisting essentially of:
 a surfactant system consisting essentially of an anionic surfactant and a zwitterionic surfactant;
 a preservative;
 a pH modifier; and
 a rheology modifier,
 wherein the ratio of anionic surfactant to zwitterionic surfactant is about 1:1 to about 2.2:1 of the total composition by weight The present disclosure provides additional exemplary embodiments, including:

1.1 Composition 1, wherein the composition is substantially free of other anionic surfactants.

1.2 Composition 1 or 1.1, wherein the composition is substantially free of other zwitterionic surfactants.

1.3 Any of compositions 1 or 1.1-1.2, wherein the composition is substantially free of other surfactants.

1.4 Any of Compositions 1 or 1.1-1.3, wherein the ratio of anionic surfactant to zwitterionic surfactant is about 1.2:1 to about 2.1:1, about 1.4:1 to about 2.1:1, or about 1.5:1 to about 2:1, about 1.6:1, about 1.8:1, or about 1.7:1 of the total composition by weight.

1.5 Any of Compositions 1 or 1.1-1.4, wherein the anionic surfactant is selected from alkyl ether sulfates, for example linear $C_8$-$C_{18}$ alkyl ether sulfates, and sodium, potassium, ammonium, and ethanolammonium salts thereof.

1.6 Any of Compositions 1 or 1.1-1.5, wherein the anionic surfactant is selected from sodium laureth sulfate, sodium lauryl sulfate, ammonium lauryl sulfate.

1.7 Any of Compositions 1 or 1.1-1.6, wherein the anionic surfactant is sodium laureth sulfate.

1.8 Any of Compositions 1 or 1.1-1.7, wherein the zwitterionic surfactant is a quaternary ammonium carboxylate betaine.

1.9 Any of Compositions 1 or 1.1-1.8, wherein the zwitterionic surfactant is cocoamidopropyl betaine.

1.10 Any of Compositions 1 or 1.1-1.9, wherein the pH modifier is selected from lactic acid, citric acid, hydrochloric acid, glycolic acid, sodium hydroxide, potassium chloride, monosodium citrate, disodium citrate, monosodium malate, sodium carbonate, bicarbonates, sesquicarbonates, borates, silicates, monosodium phosphate, trisodium phosphate, pyrophosphate salts, imidazole, or combinations thereof.

1.11 Any of Compositions 1 or 1.1-1.10, wherein the pH modifier comprises lactic acid.

1.12 Any of Compositions 1 or 1.1-1.11, wherein the rheology modifier is an inorganic salt.

1.13 Any of Compositions 1 or 1.1-1.12, wherein the rheology modifier is sodium chloride.

1.14 Any of Compositions 1 or 1.1-1.13, wherein the preservative is selected from sodium benzoate; sodium salicylate; benzalkonium chloride; benzethonium chloride; 5-bromo-5-nitro-1,3-dioxane; 2-bromo-2-nitropropane-1,3-diol; alkyl trimethyl ammonium bromide; N-(hydroxymethyl)-N-(1,3-dihydroxy methyl-2,5-dioxo-4-imidaxolidinyl-N-(hydroxy methyl)urea; 1-3-dimethyol-5,5-dimethyl hydantoin; formaldehyde; iodopropynl butyl carbamate, butyl paraben; ethyl paraben; methyl paraben; propyl paraben, methyl isothiazolinone, methyl-chloroisothiazoline; phenoxyethanol; tris-hydroxyethyl-hexahydrotriaz-ine; methylisothiazolinone; 5-chloro-2-methyl-4-isothiazolin-3-one; 1,2-dibromo-2,4-dicyanobutane; 1-(3-chloroalkyl)-3,5,7-triaza-azoniaadam-antane chloride; organic acids; or combinations thereof.

1.15 Any of Compositions 1 or 1.1-1.14, wherein the preservative is sodium benzoate.

1.16 Any of Compositions 1 or 1.1-1.15, wherein the surfactant system comprises about 5 wt % to about 15 wt %, about 7 wt % to about 12 wt %, about 8 wt % to about 10 wt %, about 8.75 wt % or about 10 wt % of active in the composition.

1.17 Any of Compositions 1 or 1.1-1.16, wherein the composition is in the form of a liquid hand soap, shower gel, body wash, bath foam, shampoo, liquid face soap, dish soap, body wash, dermal cream, or liquid detergent.

1.18 Any of Compositions 1 or 1.1-1.17, wherein the composition is in the form of a shower gel, liquid hand soap or a body wash.

1.19 Any of Compositions 1 or 1.1-1.18, further comprising one or more optional ingredients selected from a fragrance; skin conditioning agent; moisturizing agents; dyes; pigments; chelating agents; sunscreen active ingredients; antiaging compounds; antioxidants; vitamins; essential oils; or combinations thereof.

1.20 Any of Compositions 1 or 1.1-1.19, wherein the personal care composition consists essentially of a surfactant system comprising cocoamidopropyl betaine and an anionic surfactant; a preservative; an effective amount of lactic acid; and sodium chloride, wherein the ratio of anionic surfactant to cocoamidopropyl betaine is about 1.2:1 to about 2.1:1, about 1.4:1 to about 2.1:1, or about 1.5:1 to about 2:1, about 1.6:1, about 1.8:1, or about 1.7:1 of the total composition by weight.

1.21 Any of Compositions 1 or 1.1-1.20, wherein the surfactant system consists of cocoamidopropyl betaine and sodium laureth sulfate; the preservative is sodium benzoate; the pH modifier is lactic acid; and the rheology modifier is sodium chloride, wherein the ratio of sodium laureth sulfate to cocoamidopropyl betaine is about 1.2:1 to about 2.1:1, about 1.4:1 to about 2.1:1, or about 1.5:1 to about 2:1, about 1.6:1, about 1.8:1, or about 1.7:1 of the total composition by weight.

1.22 Any of Compositions 1 or 1.1-1.21, wherein the composition further includes one or more ingredients selected from among:

(a) Humectants (e.g., glycerin, sorbitol, propylene glycol), (b) Fatty acids (e.g., caproic acid, caprylic acid, capric acid, lauric acid, myristic acid, palmitic acid, palmitoleic acid, stearic acid, oleic acid, linolenic acid, linoleic acid, arachidic acid, arachidonic acid), (c) Fatty alcohols (e.g., cetearyl alcohol, cetyl alcohol, stearyl alcohol, oleyl alcohol), (d) Esters of fatty acids (e.g., esters of caproic acid, caprylic acid, capric acid, lauric acid, myristic acid, palmitic acid, palmitoleic acid, stearic acid, oleic acid, linolenic acid, linoleic acid, arachidic acid, arachidonic acid, with alcohols such as glycerol, propylene glycol, sorbitan, isopropyl alcohol, caproic alcohol, capryl alcohol, capric alcohol, lauryl alcohol, myristyl alcohol, cetearyl alcohol, cetyl alcohol, palmoleyl alcohol, stearyl alcohol, oleyl alcohol, linoyl alcohol, linolenyl alcohol, arachidyl alcohol, arachidonyl alcohol) such as isopropyl myristate, capryl stearate, isopropyl olivate, cetearyl olivate, cetearyl oleate, glyceryl caprylate, glyceryl stearate citrate, and sorbitan olivate), natural and synthetic triglycerides (e.g., di- or tri-glycerides of fatty acids, such as glyceryl caprate or caprylic/capric triglyceride), (e) Natural fats and oils (e.g., vegetable oil, coconut oil, sesame oil, avocado oil, corn oil, castor oil, shea butter, cocoa butter, soybean oil, sunflower oil, safflower oil, olive oil and tallow), (f) Emulsifiers (e.g. polyethylene glycol esters, fatty alcohol polyglycol ethers, fatty acid polyglycol ethers, polyglycerol fatty acid esters, sorbitol, sorbitan, and mono- and di-fatty acid esters of sorbitan), (g) Sunscreen actives (e.g., titanium dioxide, zinc oxide, and UV absorption inhibitors, such as octyl methoxy cinnamate, benzophenone-3, and methylene bis-benzotriazolyl tetramethyl butyl phenol), (h) Vitamins (e.g., vitamin A, vitamin E, esters of vitamin A or vitamin E, such as vitamin E acetate and retinyl palmitate).

1.23 Any of Compositions 1 or 1.1-1.22, wherein the composition is a surfactant based gel for the skin (e.g., face, hands, feet, etc.).

1.24 Any of Compositions 1 or 1.1-1.23, further comprising inorganic salts, perfumes, colorants, opacifiers, pearlizers, or any combination thereof.

1.25 Any of Compositions 1 or 1.1-1.24, wherein the composition is a cosmetic-removal product, hair care product, skin care product or personal cleansing product (e.g., liquid soaps, foams, gels, and lotions).

1.26 Any of Compositions 1 or 1.1-1.25, further comprising natural biological extracts, such as essential oils or fragrances (e.g., Amyris oil, cedarwood oil, cocoa absolute, copaiba balsam, menthe oil pays, myrrh resin, patchouli oil, vanillin, vetiver oil, Aloe extract, lemon extract, orange extract, mandarin extract, and oil or extract of anise, clove, basil, aniseed, cinnamon, geranium, rose, mint, lavender, thyme, rosemary, citronella, cypress, *eucalyptus*, peppermint, and sandalwood).

1.27 Any of Compositions 1 or 1.1-1.26, further comprising water, e.g., from 5-95% water by weight of the composition, for example, 15%-95%, 20%-95%, 25%-95%, 25%-90%, 30%-90%, 40%-90%, 50%-90%, 65%-90%, or 70-90%, or about 90%, or about 88%, or about 86%, or about 84%.

1.28 Any of Compositions 1 or 1.1-1.27, wherein the pH of the composition is from 1-8, for example, from 3.0-7.0, from 4.0-6.0, from 5.0-5.4, or about 4.2-4.8.

In a second exemplary embodiment, the invention includes a personal care composition (Composition 2) comprising:
 a surfactant system consisting essentially of an anionic surfactant and a zwitterionic surfactant;
 a preservative;
 a pH modifier; and
 a rheology modifier,
wherein the ratio of anionic surfactant to zwitterionic surfactant is about 1:1 to about 2.2:1 of the total composition by weight.

The present disclosure provides additional exemplary embodiments, including:

2.1 Composition 2, wherein the composition is substantially free of other anionic surfactants.

2.2 Composition 2 or 2.1, wherein the composition is substantially free of other zwitterionic surfactants.

2.3 Any of compositions 2 or 2.1-2.2, wherein the composition is substantially free of other surfactants.

2.4 Any of Compositions 2 or 2.1-2.3, wherein the ratio of anionic surfactant to zwitterionic surfactant is about 1.2:1 to about 2.1:1, about 1.4:1 to about 2.1:1, or about 1.5:1 to about 2:1, about 1.5:1, about 1.6:1 to about 1.8:1, or about 1.7:1, of the total composition by weight.

2.5 Any of Compositions 1 or 1.1-1.4, wherein the anionic surfactant is selected from alkyl ether sulfates, for example linear $C_8$-$C_{18}$ alkyl ether sulfates, and sodium, potassium, ammonium, and ethanolammonium salts thereof.

2.6 Any of Compositions 2 or 2.1-2.5, wherein the anionic surfactant is selected from sodium laureth sulfate, sodium lauryl sulfate, ammonium lauryl sulfate.

2.7 Any of Compositions 2 or 2.1-2.5, wherein the anionic surfactant is sodium laureth sulfate.

2.8 Any of Compositions 2 or 2.1-2.7, wherein the zwitterionic surfactant is a quaternary ammonium carboxylate betaine.

2.9 Any of Compositions 2 or 2.1-2.8, wherein the zwitterionic surfactant is cocoamidopropyl betaine.

2.10 Any of Compositions 2 or 2.1-2.9, wherein the pH modifier is selected from lactic acid, citric acid, hydrochloric acid, glycolic acid, sodium hydroxide, potassium chloride, monosodium citrate, disodium citrate, monosodium malate, sodium carbonate, bicarbonates, sesquicarbonates, borates, silicates, monosodium phosphate, trisodium phosphate, pyrophosphate salts, imidazole, or combinations thereof.

2.11 Any of Compositions 2 or 2.1-2.10, wherein the pH modifier comprises lactic acid.

2.12 Any of Compositions 2 or 2.1-2.11, wherein the rheology modifier is an inorganic salt.

2.13 Any of Compositions 2 or 2.1-2.12, wherein the rheology modifier is sodium chloride.

2.14 Any of Compositions 2 or 2.1-2.13, wherein the preservative is selected from sodium benzoate, sodium salicylate, benzalkonium chloride; benzethonium chloride, 5-bromo-5-nitro-1,3-dioxane; 2-bromo-2-nitropropane-1,3-diol; alkyl trimethyl ammonium bromide; N-(hydroxymethyl)-N-(1,3-dihydroxy methyl-2,5-dioxo-4-imidaxolidinyl-N-(hydroxy methyl)urea; 1-3-dimethyol-5,5-dimethyl hydantoin; formaldehyde; iodopropynyl butyl carbamate, isobutyl paraben; ethyl paraben; methyl paraben; propyl paraben, methyl isothiazolinone, methyl-chloroisothiazoline; phenoxyethanol; tris-hydroxyethyl-hexahydrotriazine; methylisothiazolinone; 5-chloro-2-methyl-4-isothiazolin-3-one; 1,2-dibromo-2,4-dicyanobutane; 1-(3-chloroalkyl)-3,5,7-triaza-azoniaadamantane chloride; organic acids; or combinations thereof.

2.15 Any of Compositions 2 or 2.1-2.14, wherein the preservative is sodium benzoate.

2.16 Any of Compositions 2 or 2.1-2.15, wherein the surfactant system comprises about 5 wt % to about 15 wt %, about 7 wt % to about 12 wt %, about 8 wt % to about 10 wt %, about 8.75 wt % or about 10 wt % of the composition.

2.17 Any of Compositions 2 or 2.1-2.16, wherein the composition is in the form of a liquid hand soap, shower gel, body wash, bath foam, shampoo, liquid face soap, dish soap, body wash, dermal cream, or liquid detergent.

2.18 Any of Compositions 2 or 2.1-2.17, wherein the composition is in the form of a shower gel, liquid hand soap or a body wash.

2.19 Any of Compositions 2 or 2.1-2.18, further comprising one or more optional ingredients selected from a fragrance; skin conditioning agent; moisturizing agents; dyes; pigments; chelating agents; sunscreen active ingredients; antiaging compounds; antioxidants; vitamins; essential oils; or combinations thereof.

2.20 Any of Compositions 2 or 2.1-2.19, wherein the personal care composition consists essentially of a surfactant system comprising cocoamidopropyl betaine and an anionic surfactant; a preservative; an effective amount of lactic acid; and sodium chloride, wherein the ratio of anionic surfactant to cocoamidopropyl betaine is about 1:1 to about 2.2:1, about 1.4:1 to about 2.1:1, or about 1.5:1 to about 2:1, about 1.6:1, about 1.8:1, or about 1.7:1 of the total composition by weight.

2.21 Any of Compositions 2 or 2.1-2.20, wherein the surfactant system consists of cocoamidopropyl betaine and sodium laureth sulfate; the preservative is sodium benzoate; the pH modifier is lactic acid; and the rheology modifier is sodium chloride, wherein the ratio of sodium laureth sulfate to cocoamidopropyl betaine is about 1:1 to about 2.2:1, about 1.4:1 to about 2.1:1, or about 1.5:1 to about 2:1, about 1.6:1, about 1.8:1, or about 1.7:1 of the total composition by weight.

2.22 Any of Compositions 2 or 2.1-2.21, wherein the composition further comprises one or more ingredients selected from among:

(a) Humectants (e.g., glycerin, sorbitol, propylene glycol), (b) Fatty acids (e.g., caproic acid, caprylic acid, capric acid, lauric acid, myristic acid, palmitic acid, palmitoleic acid, stearic acid, oleic acid, linolenic acid, linoleic acid, arachidic acid, arachidonic acid), (c) Fatty alcohols (e.g., cetearyl alcohol, cetyl alcohol, stearyl alcohol, oleyl alcohol), (d) Esters of fatty acids (e.g., esters of caproic acid, caprylic acid, capric acid, lauric acid, myristic acid, palmitic acid, palmitoleic acid, stearic acid, oleic acid, linolenic acid, linoleic acid, arachidic acid, arachidonic acid, with alcohols such as glycerol, propylene glycol, sorbitan, isopropyl alcohol, caproic alcohol, capryl alcohol, capric alcohol, lauryl alcohol, myristyl alcohol, cetearyl alcohol, cetyl alcohol, palmoleyl alcohol, stearyl alcohol, oleyl alcohol, linoyl alcohol, linolenyl alcohol, arachidyl alcohol, arachidonyl alcohol) such as isopropyl myristate, capryl stearate, isopropyl olivate, cetearyl olivate, cetearyl oleate, glyceryl caprylate, glyceryl stearate citrate, and sorbitan olivate), natural and synthetic triglycerides (e.g., di- or tri-glycerides of fatty acids, such as glyceryl caprate or caprylic/capric triglyceride), (e) Natural fats and oils (e.g., vegetable oil, coconut oil, sesame oil, avocado oil, corn oil, castor oil, shea butter, cocoa butter, soybean oil, sunflower oil, safflower oil, olive oil and tallow), (f) Emulsifiers (e.g. polyethylene glycol esters, fatty alcohol polyglycol ethers, fatty acid polyglycol ethers, polyglycerol fatty acid esters, sorbitol, sorbitan, and mono- and di-fatty acid esters of sorbitan), (g) Sunscreen actives (e.g., titanium dioxide, zinc oxide, and UV absorption inhibitors, such as octyl methoxy cinnamate, benzophenone-3, and methylene bis-benzotriazolyl tetramethyl butyl phenol), (h) Vitamins (e.g., vitamin A, vitamin E, esters of vitamin A or vitamin E, such as vitamin E acetate and retinyl palmitate).

2.23 Any of Compositions 2 or 2.1-2.22, wherein the composition is a surfactant based gel for the skin (e.g., face, hands, feet, etc.).

2.24 Any of Compositions 2 or 2.1-2.23, further comprising inorganic salts, perfumes, colorants, opacifiers, pearlizers, or any combination thereof.

2.25 Any of Compositions 2 or 2.1-2.24, wherein the composition is a cosmetic-removal product, hair care product, skin care product or personal cleansing product (e.g., liquid soaps, foams, gels, and lotions).

2.26 Any of Compositions 2 or 2.1-2.25, further comprising natural biological extracts, such as essential oils or fragrances (e.g., Amyris oil, cedarwood oil, cocoa absolute, copaiba balsam, menthe oil pays, myrrh resin, patchouli oil, vanillin, vetiver oil, Aloe extract, lemon extract, orange extract, mandarin extract, and oil or extract of anise, clove, basil, aniseed, cinnamon, geranium, rose, mint, lavender, thyme, rosemary, citronella, cypress, *eucalyptus*, peppermint, and sandalwood).

2.27 Any of Compositions 2 or 2.1-2.26, further comprising water, e.g., from 5-95% water by weight of the composition, for example, 15%-95%, 20%-95%, 25%-95%, 25%-90%, 30%-90%, 40%-90%, 50%-90%, 65%-90%, or 70-90%, or about 90%, or about 88%, or about 86%, or about 84%.

2.28 Any of Compositions 2 or 2.1-2.27, wherein the pH of the composition is from 1-8, for example, from 3.0-7.0, from 4.0-6.0, from 5.0-5.4, or about 4.2-4.8.

In a third exemplary embodiment, the invention includes a method (Method 1) of cleansing skin comprising the steps of providing a personal care cleansing composition as described above (e.g., any of Composition 1, 1.1-1.28, 2, or 2.1-2.28);

and applying the composition to the skin to provide a cleansing effect.

The present disclosure provides additional exemplary embodiments, including:

1.1 Method 1, further comprising the step of agitating the composition on the skin sufficiently to create a volume of foam.

In some embodiments, the invention includes a method (Method 2) for preparing a personal care cleansing composition comprising combining an effective amount of a preservative, a pH modifier, and a rheology modifier with a surfactant system comprising an anionic surfactant and a zwitterionic surfactant.

In other embodiments, the personal care compositions of the present disclosure include a surfactant system that is preferably comprised of an anionic surfactant and a zwitterionic surfactant. In some embodiments, the surfactant system comprises about 4 wt % to about 15 wt %, about 7 wt % to about 12 wt %, about 8 wt % to about 11 wt %, about 8.75 wt % or about 10 wt % of the composition.

Suitable anionic surfactants include, but are not limited to, those surface-active or detergent compounds that contain an organic hydrophobic group containing generally 8 to 26 carbon atoms or generally 10 to 18 carbon atoms in their molecular structure and at least one water-solubilizing group selected from sulfonate, sulfate, and carboxylate so as to form a water-soluble detergent. Usually, the hydrophobic group will comprise a $C_8$-$C_{22}$ alkyl, or acyl group. Such surfactants are employed in the form of water-soluble salts and the salt-forming cation usually is selected from sodium, potassium, ammonium, magnesium and mono-, di- or tri-$C_2$-$C_3$ alkanolammonium, with the sodium, magnesium and ammonium cations again being the usual ones chosen.

Some examples of suitable anionic surfactants include, but are not limited to alkyl ether sulfates, for example linear $C_8$-$C_{18}$ alkyl ether sulfates, and salts thereof, preferably the sodium, potassium, ammonium, and ethanolammonium salts thereof.

Suitable anionic ether sulfates have the formula $R(OC_2H_4)_n OSO_3M$ wherein n is 1 to 12, or 1 to 5, and R is an alkyl, alkylaryl, acyl, or alkenyl group having 8 to 18 carbon atoms, for example, an alkyl group of $C_{12}$-$C_{14}$ or $C_{12}$-$C_{16}$, and M is a solubilizing cation selected from sodium, potassium, ammonium, magnesium and mono-, di- and triethanol ammonium ions. Exemplary alkyl ether sulfates contain 12 to 15 carbon atoms in the alkyl groups thereof, e.g., sodium laureth (2 EO) sulfate. Some preferred exemplary anionic surfactants that may be used in the compositions of the present disclosure include sodium laurel ether sulfate (SLES), sodium lauryl sulfate, and ammonium lauryl sulfate.

Preferably, the present compositions comprise a single anionic surfactant. In some embodiments, the anionic surfactant is present in an amount of about 0.01 wt % to about 20 wt %, about 0.1 wt % to about 10 wt %, about 3 wt % to about 10 wt %, about 2 wt % to about 8 wt %, about 3 wt % to about 8 wt %, about 4 wt % to about 9 wt %, or about 5 wt % to about 7 wt %.

In some embodiments, the personal care compositions of the present disclosure include a zwitterionic surfactant. Suitable zwitterionic surfactants include betaines and sultaines. In some embodiments, the zwitterionic surfactant comprises a betaine having a quaternary ammonium or phosphonium ion as the cationic group and a carboxylate group as the anionic group; for comprises a betaine having a quaternary ammonium ion as the cationic group and a carboxylate group as the anionic group (i.e., a quaternary ammonium carboxylate betaine). Typical alkyldimethyl betaines include, but are not limited to, decyl dimethyl betaine or 2-(N-decyl-N, N-dimethylammonia)acetate, coco dimethyl betaine or 2-(N-coco N, N-dimethylammonia) acetate, myristyl dimethyl betaine, palmityl dimethyl betaine, lauryl dimethyl betaine, cetyl dimethyl betaine, stearyl dimethyl betaine, etc. The amidobetaines similarly include, but are not limited to, cocoamidoethylbetaine, cocoamidopropyl betaine and the like. In one embodiment, the betaine is coco ($C_8$-$C_{18}$) amidopropyl dimethyl betaine. Two examples of betaine surfactants that can be used are EMPIGEN™ BS/CA from Huntsman, and Tegobetaine F50 from BASF. Other suitable zwitterionic surfactants include amine oxides.

The compositions of the present disclosure preferably comprise a single zwitterionic surfactant. In some embodiments, the zwitterionic surfactant is present in an amount of about 0.01 wt % to about 10 wt %, about 1 wt % to about 9 wt %, about 1 wt % to about 5 wt %, about 3 wt % to about 5 wt %, about 4 wt % to about 12 wt %, about 2.5 wt % to about 5 wt %, or about 3 wt % to about 4 wt %.

In some embodiments, the surfactant system comprises an anionic surfactant and a zwitterionic surfactant in a weight ratio of about 1:3 to about 3:1. In some embodiments, the ratio of anionic:zwitterionic surfactant is about 2:1 to about 1:2, about 1:1 to about 2.3:1, about 1.2:1 to about 2.1:1, about 1.4:1 to about 2.1:1, about 1.5:1 to about 2:1; about 1.6:1 to about 1.8:1, or about 1.7:1, of the total composition by weight; for example about 1:1, about 1.1:1, about 1.2:1, about 1.3:1, about 1.4:1, about 1.5:1, about 1.6:1, about 1.7:1, about 1.8:1, about 1.9:1, about 2:1, about 2.1:1, about 2.2:1, about 2.3:1, about 2.4:1, or about 2.5:1.

In some embodiments, preservatives are included in the composition, preferably at a concentration of about 0.01 wt % to about 10 wt %, about 0.01 wt % to 3 wt %, or 0.01 wt % to 2.5 wt %. Examples of preservatives include, but are not limited to, benzalkonium chloride; sodium salicylate; benzethonium chloride, 5-bromo-5-nitro-1,3 dioxane; 2-bromo-2-nitropropane-1,3-diol; alkyl trimethyl ammonium bromide; N-(hydroxymethyl)-N-(1,3-dihydroxy methyl-2,5-dioxo-4-imidaxolidinyl-N-(hydroxy methyl) urea; 1-3-dimethyol-5,5-dimethyl hydantoin; formaldehyde; iodopropynl butyl carbamate, butyl paraben; ethyl paraben; methyl paraben; propyl paraben, mixture of methyl isothiazolinone/methyl-chloroisothiazoline in a 1:3 wt. ratio; mixture of phenoxyethanol/butyl paraben/methyl paraben/propylparaben; 2-phenoxyethanol; tris-hydroxyethyl-hexahydrotriazine; methylisothiazolinone; 5-chloro-2-methyl-4-isothiazolin-3-one; 1,2-dibromo-2,4-dicyanobutane; 1-(3-chloroalkyl)-3,5,7-triaza-azoniaadamantane chloride; sodium benzoate, sodium salicylate; organic acids, lactic acid, or citric acid and combinations thereof.

pH modifying agents include acidifying agents to lower pH, basifying agents to raise pH and buffering agents to control pH within a desired range. For example, one or more compounds selected from acidifying, basifying and buffering agents can be included to provide a pH of 2 to 10, or in various illustrative embodiments 2 to 8, 3 to 9, 4 to 8, 5 to 7, 6 to 10, 7 to 9, etc. In preferred embodiments, the pH is between about 1 to 5, about 2 to 5, about 4 to 5, or about 4.2-4.8. Examples of pH modifying agent include HCl, phosphoric and sulfonic acids and carboxylic acids such as lactic acid and citric acid, acid salts (e.g., monosodium citrate, disodium citrate, monosodium malate, etc.), alkali metal hydroxides such as sodium hydroxide and potassium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and the like. One or more pH modifying agents are optionally present in a total amount effective to maintain the composition in an acceptable pH range. Preferably, only one pH modifying agent is employed.

In certain embodiments, the personal care composition is in the form of a cleansing liquid.

In some embodiments, personal care compositions of the present disclosure can optionally include an emollient component. Illustrative examples of such emollient components include glycerine, glyceryl oleate, caprylyl glycol, triglycerides (e.g., caprylic/capric triglyceride), silicone oils (e.g., cyclomethicone), ester oils (e.g., butyl myristate, isopropyl myristate, cetyl myristate, isopropyl palmitate, isopropyl stearate, octyl stearate, isocearyl stearate), organic fatty alcohols (e.g., oleic alcohol, linolenic alcohol, linoleic alcohol, isostearyl alcohol, octyl dodecanol).

In some embodiments, personal care compositions of the present disclosure further include one or more optional ingredients selected from coloring agents, fragrances, moisturizing agents, and amino acids.

In some embodiments, personal care compositions of the present disclosure comprise a rheology modifier, useful for example to inhibit settling or separation of ingredients or to promote acceptable usage experience. In some embodiments, the rheology modifier is selected from an inorganic salt, isopropyl palmitate, isopropyl myristate, a polymer, salts or other electrolytes such as e.g., sodium chloride, and other mono-, di- and trivalent salts, and a hydrotrope. In some embodiments, the rheology modifier includes a brine solution comprising sodium chloride. One or more rheology modifiers are optionally present in a total amount of 0.01 wt % to 10 wt %, for example 0.1 wt % to 8 wt % or about 0.01 wt % to about 6 wt % of the composition.

Further optional ingredients can also be present in the personal care composition, although it is generally preferably to limit the ingredients to the minimal ingredients described above. Non-limiting examples of further optional ingredients include skin conditioning agents, moisturizing agents, fragrance, dyes and pigments, titanium dioxide, chelating agents such as EDTA, sunscreen active ingredients such as butyl methoxy benzoylmethane; antiaging compounds such as alpha hydroxy acids, beta hydroxy acids; antioxidants such as butylated hydroxytoluene (BHT); vitamins such as A, E, K and C; essential oils and extracts thereof such as rosewood and jojoba, free fatty acids to provide enhanced skin feel benefits such as softer or smoother feeling skin, for example free fatty acids include those derived from tallow, coconut oil, palm oil and palm kernel oil, and mixtures of any of the foregoing components.

In some embodiments, the personal care composition optionally includes fragrance in an amount of about 0.01 wt % to about 4 wt % by weight of the composition, preferably about 0.1 wt % to about 2 wt %, more preferably about 0.2 wt % to about 1.5 wt %.

In some embodiments, the personal care composition optionally includes pearlizers, such as Styrene/Acrylates Copolymer or glycol distearate, in an amount of about 0.01 wt % to 3 wt % by weight.

The personal care compositions of the present disclosure may be prepared by any ordinary methods known in the art. For example, the composition may be prepared by mixing the anionic surfactant into a suitable aqueous carrier. The components are mixed for a period of time sufficient for complete incorporation. Once mixture is complete, the zwitterionic surfactant is added to the mixture, and the components are again mixed for a suitable period of time. Following addition of the surfactants, a preservative is added with an accompanying appropriate mixing process. A pH modifier is added to the mixture until desired pH level is achieved. A rheology modifier is added to achieve a desired viscosity, and the final mixture is mixed for an appropriate amount of time until the ingredients are homogenously dispersed.

Exemplary embodiments of the present disclosure will be illustrated by reference to the following examples, which are included to exemplify, but not to limit the scope of the present invention.

EXAMPLES

Example 1

Table 1 describes the formula of an exemplary composition according to the present disclosure.

TABLE 1

| Ingredient | Composition I (wt %) |
| --- | --- |
| Water | 72.5 |
| Sodium Laureth Sulfate | 7.9 |
| Cocoamidopropyl Betaine | 10.8 |
| Sodium Benzoate | 0.4 |

TABLE 1-continued

| Ingredient | Composition I (wt %) |
|---|---|
| Lactic Acid | 0.5 |
| Sodium Chloride | 0.4 |

The exemplary composition described in Table 1 (above) may be prepared according to conventional methods known to those skilled in the art. In particular, the exemplary composition of the present invention is prepared to ensure that the surfactant system provides the anionic and zwitterionic surfactants at certain weight ratios. The sodium laureth sulfate is provided in the form of a diluted solution containing 70% by weight of sodium laureth sulfate; the cocoamidopropyl betaine is provided in the form of a diluted solution containing 30% by weight of cocoamidopropyl betaine; and the lactic acid is provided in the form of a diluted solution containing 50% by weight of lactic acid.

Example 2

A comprehensive study is conducted on Composition I to evaluate its rheological parameters. The tests are carried out on a Brookfield DV-II+ Viscometer. The study tested the viscosity of variants of Composition I having varied amounts of sodium chloride brine solution and varied ratios of anionic surfactant to zwitterionic surfactant.

The surfactant system includes sodium laureth sulfate as the anionic surfactant and cocoamidopropyl betaine as the zwitterionic surfactant. Five formulations are tested: Composition II has an anionic:zwitterionic ratio of 1.3:1; Composition III has an anionic:zwitterionic ratio of 1.5:1; Composition IV has an anionic:zwitterionic ratio of 2:1; Composition V has an anionic:zwitterionic ratio of 3:1; and Composition VI has an anionic:zwitterionic ratio of 4.2:1. Each of the formulations are subjected to increasingly greater concentrations of sodium chloride brine solution to observe the effect on viscosity. It is found that Composition III and IV unexpectedly showed acceptable viscosities at a wide range of sodium chloride brine solution concentrations for extended periods of time. Acceptable viscosity is considered to be between 4000 mPa*s and 7000 mPa*s.

Composition III exhibits a favorable viscosity profile with as little as 1 wt % and as much as 5 wt % sodium chloride brine solution added. Composition IV showed a favorable viscosity profile with a range of 3 wt % to about 5 wt % brine solution added. Both Composition III and IV maintain favorable viscosity profiles after prolonged storage. Composition II shows a favorable viscosity immediately upon mixing, but does not meet consumer acceptable rheological standards. Compositions V and VI show unacceptably low viscosities and have extremely watery consistencies. Composition V requires very high concentrations of sodium chloride brine solution to be brought to an acceptable viscosity, and Composition VI never achieves acceptable viscosity, even with large amounts of brine solution added.

Example 3

Based on the results obtained in Example 2 above, four additional formulations are prepared having varied ratios of anionic surfactant to zwitterionic surfactant and concentrations of the surfactant system. Composition VII has a surfactant ratio of 1.5:1 and a surfactant system comprising 8.75 wt % of the composition. Composition VIII has a surfactant ratio of 1.7:1 and a surfactant system comprising 8.75 wt % of the composition. Composition IX has a surfactant ratio of 1.7:1 and a surfactant system comprising 10 wt % of the composition. Composition X has a surfactant ratio of 2:1 and a surfactant system comprising 10 wt % of the composition. Compositions VI to IX produced acceptable viscosities when subjected to the test described above.

A foam profile evaluation was conducted on each of Compositions VII to X. The tests are carried out on a SITA Foam Tester R-2000. 250 mL samples of each of the compositions are prepared and subjected to agitation for equal periods at a temperature of 40° C. to simulate normal conditions during use, for example, in a shower. Each of the tested formulations show foam generation. In the tests, Compositions VII to X and a Comparative Example (Comp. Ex. I) having significantly more ingredients, are each subjected to agitation for a period of 80 seconds, and a Foam Generated parameter is calculated as the slope of the linear plot of foam generation over time. The results are summarized in Table 2 (below).

TABLE 2

| Sample | Foam Generated |
|---|---|
| Composition VII | 10.2 |
| Composition VIII | 11.1 |
| Composition IX | 10.75 |
| Composition X | 11.3 |
| Comp. Ex. I | 11.4 |

The results described in Table 2 (above) demonstrate that Compositions VI to IX provide high foam generation rates that are parity to Comp. Ex I. This data demonstrates that exemplary compositions of the present invention are unexpectedly able to generate foam at a similar rate to a composition having significantly more ingredients (Comp. Ex. I), despite having a limited number of ingredients.

Example 4

Compositions VII to X are subjected to evaluation of sensory properties by a U.S. Sensory Spectrum Expert Sensory Panel. The formulations are tested for lather during washing, wet skin feel after washing, skin feel after drying, and product texture and consistency. The results are summarized below in Tables 3-9 (below).

TABLE 3

| Comparison of Composition VII to Comp. Ex. I | |
|---|---|
| Test | Qualities Observed |
| Lather during washing | Higher amount of lather on pouf |
| | Lower in the amount of lather at 20 and 30 laps |
| | Lower in lather thickness |
| Wet skin feel after washing | No differences observed |
| Skin feel after drying | No differences observed |
| Product texture and consistency | Higher in shape integrity immediately after pour and 10-seconds thereafter |
| | Lower in cohesiveness |
| | Lower in firmness |
| | Lower in stickiness |

TABLE 4

Comparison of Composition VIII to Comp. Ex. I

| Test | Qualities Observed |
| --- | --- |
| Lather during washing | Higher amount of lather on pouf |
| Wet skin feel after washing | No differences observed |
| Skin feel after drying | No differences observed |
| Product texture and consistency | Higher in peaking<br>Higher in shape integrity immediately after pour and 10-seconds thereafter<br>Lower in cohesiveness<br>Lower in firmness<br>Lower in stickiness |

TABLE 5

Comparison of Composition IX to Comp. Ex. I

| Test | Qualities Observed |
| --- | --- |
| Lather during washing | Higher amount of lather on pouf |
| Wet skin feel after washing | No differences observed |
| Skin feel after drying | No differences observed |
| Product texture and consistency | Lower in cohesiveness<br>Lower in firmness<br>Lower in stickiness |

TABLE 6

Comparison of Composition X to Comp. Ex. I

| Test | Qualities Observed |
| --- | --- |
| Lather during washing | No differences observed |
| Wet skin feel after washing | No differences observed |
| Skin feel after drying | No differences observed |
| Product texture and consistency | Lower in cohesiveness<br>Lower in firmness<br>Lower in stickiness |

TABLE 7

Comparison of Composition VII to Compositions VIII, IX and X

| Test | Qualities Observed |
| --- | --- |
| Lather during washing | Higher amount of lather on pouf compared to Composition IX<br>Lower in the amount of lather at 20 and 30 laps compared to Formulations 8 and 9<br>Lower in lather thickness compared to Compositions IX and X |
| Wet skin feel after washing | No differences observed |
| Skin feel after drying | Lower in moistness at 5-minutes and 10-minutes after drying compared to Composition X |
| Product texture and consistency | Higher in peaking compared to Composition IX<br>Higher in shape integrity immediately after pour and 10 seconds thereafter compared to Compositions VIII, IX and X<br>Higher in cohesiveness compared to Compositions VIII, IX and X |

TABLE 8

Comparison of Composition VIII to Compositions IX and X

| Test | Qualities Observed |
| --- | --- |
| Lather during washing | Lower in the amount of lather at 30 laps compared to Composition IX<br>Lower in lather thickness compared to Composition IX |
| Wet skin feel after washing | No differences observed |
| Skin feel after drying | Lower in moistness at 5-minutes and 10-minutes after drying compared to Composition X |
| Product texture and consistency | Higher in peaking compared to Composition IX<br>Higher in cohesiveness compared to Composition IX |

TABLE 9

Comparison of Composition IX to Composition X

| Test | Qualities Observed |
| --- | --- |
| Lather during washing | No differences observed |
| Wet skin feel after washing | No differences observed |
| Skin feel after drying | Lower in moistness at 5-minutes and 10-minutes after drying compared to Composition X |
| Product texture and consistency | Lower in peaking compared to Composition X<br>Lower in cohesiveness compared to Composition X |

As illustrated by the data described in Tables 3 to 9 (above), Compositions VII to X have sensory properties that are comparable with Comp. Ex. I. Each of the formulations provide greater lather than Comp. Ex. I. In addition, Composition X was found to have greater moisturizing properties than Compositions VII to IX. These results are truly unexpected given the limited number of ingredients that are used in the exemplary compositions of the present invention.

The invention has been described above with reference to illustrative Examples, but it is to be understood that the invention is not limited to the disclosed embodiments. Alterations and modifications that would occur to one of skill in the art upon reading the specification are also within the scope of the invention, which is defined in the appended claims.

What is claimed is:

1. A personal care composition comprising:
    a surfactant system consisting essentially of an anionic surfactant sodium laureth sulfate and a zwitterionic surfactant cocoamidopropyl betaine;
    a preservative the comprises sodium benzoate;
    a pH modifier that comprises lactic acid; and
    a rheology modifier that comprises sodium chloride,
    wherein the rheology modifier is present in a total amount of 0.01 wt % to 10 wt % of the personal care composition, and
    wherein the weight ratio of sodium laureth sulfate to cocamidopropyl betaine is from about 1:6 to about 1:8.

2. The personal care composition of claim 1, wherein the composition is free of other anionic surfactants.

3. The personal care composition of claim 1, wherein the composition is free of other zwitterionic surfactants.

4. The personal care composition of claim 1, wherein the composition is free of other surfactants.

5. The personal care composition of claim 1, wherein the pH modifier further comprises a compound selected from citric acid, hydrochloric acid, glycolic acid, sodium hydroxide, potassium chloride, monosodium citrate, disodium citrate, monosodium malate, sodium carbonate, bicarbonates, sesquicarbonates, borates, silicates, monosodium phosphate, trisodium phosphate, pyrophosphate salts, imidazole, and a combination of two or more thereof.

6. The personal care composition of claim 1, wherein the preservative further comprises a compound selected from sodium salicylate; benzalkonium chloride; benzethonium chloride; 5-bromo-5-nitro-1,3-dioxane; 2-bromo-2-nitropropane-1,3-diol; alkyl trimethyl ammonium bromide; N-(hydroxymethyl)-N-(1,3-dihydroxy methyl-2,5-dioxo-4-imidaxolidinyl-N-(hydroxy methyl)urea; 1-3-dimethyol-5,5-dimethyl hydantoin; formaldehyde; iodopropynyl butyl carbamate, butyl paraben; ethyl paraben; methyl paraben; propyl paraben, methyl isothiazolinone, methyl-chloroisothiazoline; phenoxyethanol; tris-hydroxyethyl-hexahydrotriazine; methylisothiazolinone; 5-chloro-2-methyl-4-isothiazolin-3-one; 1,2-dibromo-2,4-dicyanobutane; 1-(3-chloroalkyl)-3,5,7-triaza-azoniaadamantane chloride; organic acids; or combinations thereof.

7. The personal care composition of claim 1, wherein the surfactant system comprises about 5 wt % to about 15 wt % of the personal care composition.

8. The personal care composition of claim 1, wherein the composition is in a form selected from a liquid hand soap, a shower gel, a body wash, a shampoo, a liquid face soap, a dish soap, a body wash, a dermal cream, and a liquid detergent.

9. The personal care composition of claim 1, further comprising one or more optional ingredients selected from a fragrance; a skin conditioning agent; a moisturizing agent; a dye; a pigment; a chelating agent; a sunscreen active ingredient; an antiaging compound; an antioxidant; a vitamin; an essential oil; and a combination of two or more thereof.

10. A method of cleansing skin comprising applying to the skin a composition according to claim 1.

* * * * *